US011179054B2

(12) United States Patent
Raudins et al.

(10) Patent No.: US 11,179,054 B2
(45) Date of Patent: Nov. 23, 2021

(54) IMAGING TO DETERMINE ELECTRODE GEOMETRY

(71) Applicant: CARDIOINSIGHT TECHNOLOGIES, INC., Independence, OH (US)

(72) Inventors: Glenn D. Raudins, Chagrin Falls, OH (US); Qingguo Zeng, Solon, OH (US); Charulatha Ramanathan, Solon, OH (US); Ryan M. Bokan, Denver, CO (US)

(73) Assignee: CARDIOINSIGHT TECHNOLOGIES, INC., Independence, OH (US)

( * ) Notice: Subject to any disclaimer, the term of this patent is extended or adjusted under 35 U.S.C. 154(b) by 581 days.

(21) Appl. No.: 16/033,971

(22) Filed: Jul. 12, 2018

(65) Prior Publication Data
US 2019/0015012 A1    Jan. 17, 2019

Related U.S. Application Data

(60) Provisional application No. 62/531,643, filed on Jul. 12, 2017.

(51) Int. Cl.
*A61B 5/0536* (2021.01)
*A61B 5/00* (2006.01)
(Continued)

(52) U.S. Cl.
CPC .......... *A61B 5/0536* (2013.01); *A61B 5/0064* (2013.01); *A61B 5/064* (2013.01);
(Continued)

(58) Field of Classification Search
CPC ...... A61B 2034/105; A61B 2034/2051; A61B 2034/2065; A61B 2090/367;
(Continued)

(56) References Cited

U.S. PATENT DOCUMENTS 10,149,618 B1 * 12/2018 Tandon ................ A61B 5/0037
2008/0232700 A1 * 9/2008 Gering ................... A61B 6/032
382/232

(Continued)

OTHER PUBLICATIONS

Applicant: CardioInsight Technologies, Inc.; International PCT Patent Application No. PCT/US2018/041834; Filed Jul. 12, 2018; International Search Report and Written Opinion; Date of Completion: Jan. 10, 2019; 14 pgs/.

(Continued)

*Primary Examiner* — Amelie R Davis
(74) *Attorney, Agent, or Firm* — Tarolli, Sundheim, Covell & Tummino LLP

(57) ABSTRACT

A method includes placing a set of electrodes on a body surface of a patient's body. The method also includes digitizing locations for the electrodes across the body surface based on one or more image frames using range imaging and/or monoscopic imaging. The method also includes estimating locations for hidden ones of the electrodes on the body surface not visible during the range imaging and/or monoscopic imaging. The method also includes registering the location for the electrodes on the body surface with predetermined geometry information that includes the body surface and an anatomical envelope within the patient's body. The method also includes storing geometry data in non-transitory memory based on the registration to define spatial relationships between the electrodes and the anatomical envelope.

20 Claims, 10 Drawing Sheets

(51) Int. Cl.
  *A61B 6/03*     (2006.01)
  *A61B 6/00*     (2006.01)
  *G06T 7/33*     (2017.01)
  *A61B 34/20*    (2016.01)
  *A61B 90/00*    (2016.01)
  *G06T 7/00*     (2017.01)
  *A61B 5/06*     (2006.01)
  *G06T 7/73*     (2017.01)
  *A61B 5/282*    (2021.01)
  *A61B 34/10*    (2016.01)

(52) U.S. Cl.
  CPC .............. *A61B 5/282* (2021.01); *A61B 6/032* (2013.01); *A61B 6/5247* (2013.01); *A61B 34/20* (2016.02); *A61B 90/361* (2016.02); *A61B 90/39* (2016.02); *G06T 7/0012* (2013.01); *G06T 7/337* (2017.01); *G06T 7/74* (2017.01); *A61B 5/4836* (2013.01); *A61B 5/684* (2013.01); *A61B 5/6805* (2013.01); *A61B 2034/105* (2016.02); *A61B 2034/2051* (2016.02); *A61B 2034/2065* (2016.02); *A61B 2090/367* (2016.02); *A61B 2090/376* (2016.02); *A61B 2090/3937* (2016.02); *A61B 2090/3966* (2016.02); *A61B 2090/3983* (2016.02); *A61B 2090/3995* (2016.02); *A61B 2562/0209* (2013.01); *A61B 2562/046* (2013.01); *G06T 7/73* (2017.01); *G06T 2207/10028* (2013.01); *G06T 2207/10081* (2013.01); *G06T 2207/30048* (2013.01); *G06T 2207/30204* (2013.01)

(58) Field of Classification Search
  CPC ...... A61B 2090/376; A61B 2090/3937; A61B 2090/3966; A61B 2090/3983; A61B 2090/3995; A61B 2562/0209; A61B 2562/046; A61B 34/20; A61B 5/0044; A61B 5/0064; A61B 5/0077; A61B 5/0536; A61B 5/064; A61B 5/282; A61B 5/367; A61B 5/4836; A61B 5/6805; A61B 5/684; A61B 5/7425; A61B 6/032; A61B 6/5247; A61B 90/361; A61B 90/39; G06T 2207/10028; G06T 2207/10081; G06T 2207/30048; G06T 2207/30204; G06T 7/0012; G06T 7/337; G06T 7/73; G06T 7/74

See application file for complete search history.

(56) References Cited

U.S. PATENT DOCUMENTS

| | | |
|---|---|---|
| 2010/0049037 A1 | 2/2010 | Pinter et al. |
| 2015/0038862 A1 | 2/2015 | Gijsbers et al. |
| 2015/0320331 A1 | 11/2015 | van Dam et al. |
| 2015/0320515 A1 | 11/2015 | Edwards et al. |
| 2016/0242697 A1 | 8/2016 | Albert |
| 2018/0235714 A1* | 8/2018 | Kuo ............. A61B 5/1114 |

OTHER PUBLICATIONS

Ghanem R. N., et al.; "Noninvasive Electrocardiographic Imaging (ECGI): Comparison to intraoperative mapping in patients"; Heart Rhythm, Elsevier, US, vol. 2, No. 4, Apr. 1, 2005; pp. 339-354, XP0027678537, ISSN: 1547-5271.

Applicant: Cardioinsight Technologies, Inc.; European Patent Application No. 18832574.0; Extended European Search Report; dated Feb. 26, 2021; 7 pgs.

* cited by examiner

IMAGING TO DETERMINE ELECTRODE GEOMETRY

CROSS-REFERENCE TO RELATED APPLICATION

This application claims the benefit of priority from U.S. provisional application No. 62/531,643, filed 12 Jul. 2017, and entitled IMAGING TO DETERMINE ELECTRODE GEOMETRY, which is incorporated herein by reference.

TECHNICAL FIELD

This disclosure relates to using imaging to determine geometry of an array of electrodes.

BACKGROUND

Electrocardiographic imaging (ECGI) is a noninvasive imaging modality for cardiac electrophysiology (EP) and arrhythmias that can be used to reconstruct epicardial potentials and to provide electrograms and isochrones from, for example, BSPMs and/or other electrocardiographic body surface potentials. To perform noninvasive Electrocardiographic Imaging (ECGI), the location and geometry of body surface electrodes are determined by placing the electrodes on a patient during a computed tomography (CT) scan or another medical imaging modality. At many healthcare facilities, this may be difficult to schedule, time consuming as well as expensive. For example, electrodes need to be placed on patient during CT scan, and the same vest needs to stay on patient until the time of the patient's EP procedure. In some examples, due to scheduling of hospitals, the waiting time between CT scan and actual EP procedure can exceed 6 hours.

SUMMARY

This disclosure relates to using imaging to determine geometry of an array of electrodes.

As one example, a method includes placing a set of electrodes on a body surface of a patient's body. The method also includes digitizing locations for the electrodes across the body surface based on one or more image frames using range imaging and/or monoscopic imaging. The method also includes estimating locations for hidden ones of the electrodes on the body surface not visible during the range imaging and/or monoscopic imaging. The method also includes registering the location for the electrodes on the body surface with predetermined geometry information that includes the body surface and an anatomical envelope within the patient's body. The method also includes storing geometry data in non-transitory memory based on the registration to define spatial relationships between the electrodes and the anatomical envelope.

As another example, a system includes an image acquisition system comprising a portable range imaging device and/or monoscopic imaging device configured to generate imaging data containing one or more image frames of a body surface including a plurality of electrodes have been positioned on the body surface and in direct line of sight during image capture by the range imaging device and/or monoscopic imaging device. Non-transitory memory stores machine readable instructions and data, the data including predetermined geometry information for an internal cardiac envelope and the body surface. At least one processor can access the memory and execute the instructions to perform a method. The method executed by the processor includes determining three-dimensional electrode locations and surface geometry from the imaging data. The determined three-dimensional electrode locations and surface geometry including estimated locations for hidden electrodes outside of the direct line of sight during image capture by the portable range imaging device and/or monoscopic imaging device. The determined three-dimensional electrode locations and surface geometry is registered with the predetermined geometry information for the cardiac envelope and the body surface to provide aggregate geometry data describing a three-dimensional spatial relationship between each of the plurality of electrodes and the cardiac envelope. The aggregate geometry data is stored in the memory.

DETAILED DESCRIPTION

Figure 1:
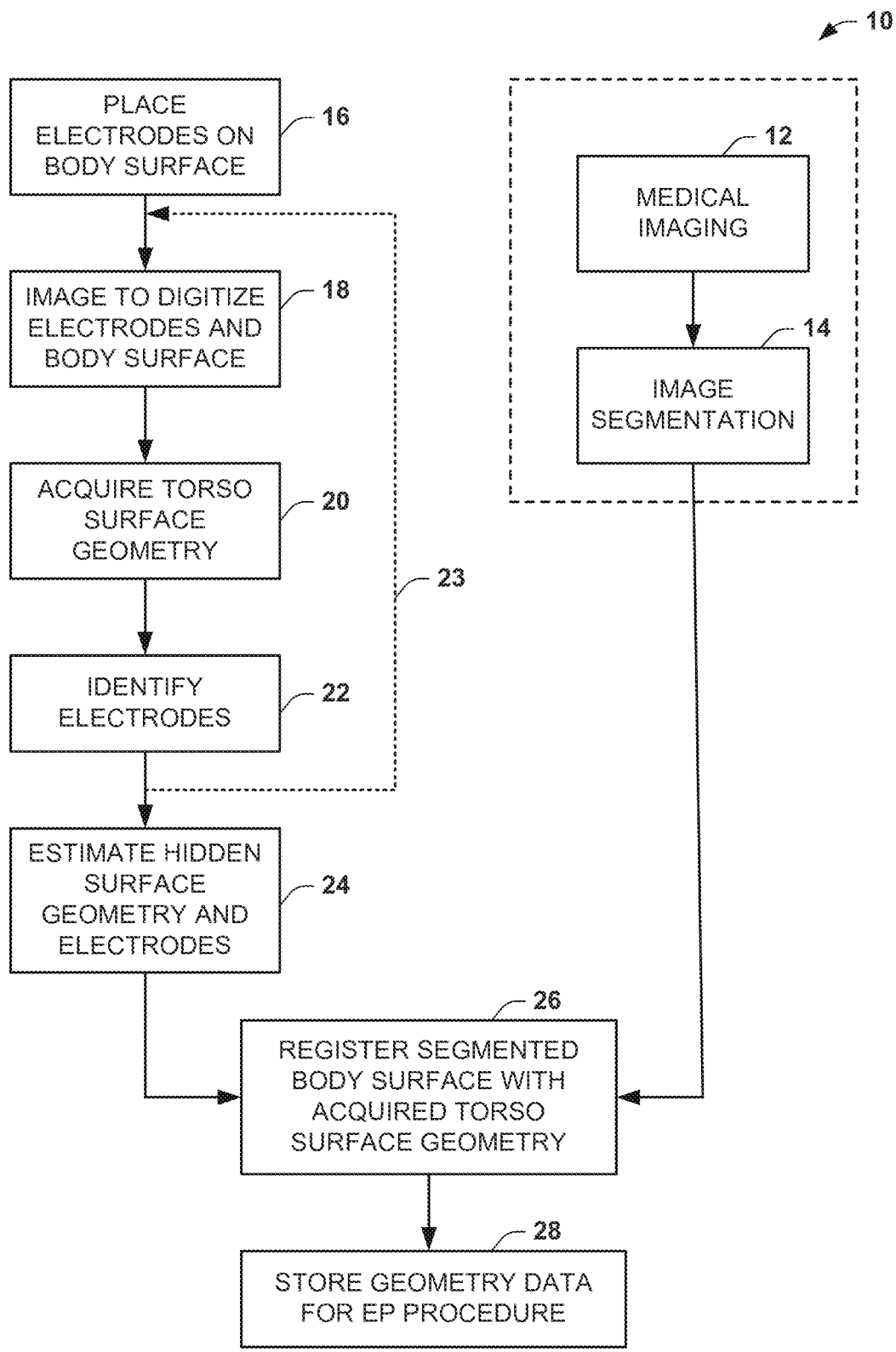
FIG. 1 depicts an example of a method for digitizing electrodes and anatomy to generate geometry data for use in an electrophysiology procedure.

This disclosure relates to using imaging (via a range imaging device and/or a monoscopic imaging device) to acquire electrode locations on a patient's body surface in a manner that can be decoupled from the method used to obtain anatomical geometry information that describes the spatial relationship of an internal anatomical envelope (a cardiac envelope such as the heart surface) and the body surface.

By way of example, instead of keeping electrodes on patient during medical imaging (e.g., via computed tomography or other imaging modality) the approach herein enables the medical imaging to be performed without electrodes on the patient. As a result, the electrodes can be placed onto patient skin at a time proximate in time to the procedure (e.g., an electrophysiology (EP) procedure). After the electrodes are positioned on the patient's body, a range imaging device (e.g., a range imaging camera or 3D scanning device) is utilized to digitize the electrodes. In another example, markers can be placed at predefined locations at or near respective electrode locations. For example, the markers can be integrated into patch, vest or other form of garment containing the array of electrodes, such that the relative spatial location of markers and electrodes is known.

After the electrodes and markers are positioned on the patient's body, optical imaging is performed (e.g., using a portable range imaging camera or monoscopic imaging device) to record a series of image frames of the electrodes to which the markers have been applied. Image processing can be performed to stitch the image frames together to align the frames and respective electrode locations in such frames. The image processing further includes estimating locations of hidden electrodes, such as may reside on a back panel while the patient is supine on a table. Regardless of which image acquisition approach (or multiple approaches) are utilized, registration is then performed on patient skin surface from the medical imaging and the electrodes and body surface digitized using optical imaging (e.g., with a range imaging or monoscopic imaging device) to provide corresponding geometry data. In some examples, a patient has pre-existing medical image for the part of the body where the electrodes are placed (e.g., CT or MRI volume for patient's torso), and system and methods disclosed herein can use these previously acquired images directly to work with images obtained using the range imaging device. This process is facilitated since the optical imaging device may be portable (e.g., a phone, tablet, handheld digital camera or other portable camera device) and readily available for use without requiring specialized training.

The approaches disclosed herein enable the medical imaging scan to be decoupled from placement of the electrodes on the patient, which affords flexibility of scheduling healthcare resources, and significantly reduce supporting burden for both suppliers and healthcare providers, meanwhile improving the quality of diagnosis. For example, the medical imaging scan can be acquired independently from placement of the electrodes on the patient. As a result of the approach disclosed herein, the patient waiting period is reduced, which likewise increase patient comfort. The approach further leads to an increase in signal quality due to potentially loose contacts, patient movement etc. that tends to occur during such long waiting periods. In the end, the approach disclosed herein helps to improve the resulting mapping quality of ECGI and patient's procedure success rate can be increased. The digitization of the electrodes on the patient's body thus can be done and electrical information acquired over a time interval (e.g., for screening purposes), with or without knowing heart geometry from other medical imaging modalities.

As used herein, the term range imaging device (e.g., camera) can refer to a number of different types of imaging devices. For example, the underlying sensing mechanism utilized by the device may include range-gated time of flight (ToF), radio frequency-modulated ToF, pulsed-light ToF, and projected-light stereo. Regardless of the sensing mechanism being implemented, the camera provides image frames with that include images (sometimes in color) and depth information for each pixel (depth images). A range imaging device is also known by other names, including flash lidar, time-of-flight (ToF) camera, and RGB-D camera, to name a few. Monoscopic imaging can include a digital optical camera that is non-depth based and capable of acquiring and reconstructing an image of a three-dimensional object (the patient) from a range of different camera viewing angles (e.g., a cell phone or other portable handheld device that includes a monoscopic camera).

As used herein, a medical imaging refers to any technique and/or process of creating visual representations of anatomy that includes the interior of a body, such as for clinical analysis and medical intervention, as well as visual representation of the function of some organs or tissues (physiology). A medical imaging device thus refers to one or more devices configured to perform medical imaging. Medical imaging thus may reveal internal structures hidden by the skin and bones. Some examples of medical imaging include devices configured to implement one or more imaging technologies comprising: X-ray radiography, fluoroscopy, medical ultrasonography or ultrasound, tomography (X-ray computed tomography (CT), positron emission tomography (PET), single-photon emission computed tomography (SPECT), magnetic resonance imaging and the like), as well as other imaging techniques. Other imaging modalities may also be utilized, individually or in combination, in other examples to provide the medical imaging.

Additionally, while many examples herein are described in the context of detection and analysis of cardiac electrical signals, it is to be understood that the approaches disclosed herein are equally applicable to determine geometry for use in solving the inverse problem for non-invasively estimating other electrophysiological signals, such as acquired as part of electroencephalography, electromyography, electrooculography and the like.

FIG. 1 depicts an example of a workflow method 10 for digitizing sensing electrodes and anatomy for use in an EP procedure. The workflow 10 allows the digitization of the geometry of electrodes to be decoupled from generating geometry for anatomy that is used as part of an EP study, as mentioned above. In the example of FIG. 1, the workflow 10 includes medical imaging 12. The medical imaging 12 can employ any medical imaging modality to image patient anatomy internally, such as disclosed herein. The workflow also involves image segmentation at 14. The segmentation at 14 thus may employ image processing determine three-dimensional geometry for body surface and an anatomical envelope (e.g., for the heart) based on the medical imaging that is performed. The anatomical geometry, for example, may be generated from the medical imaging performed at 12 to identify the relationship of the outer body surface (e.g., skin) and anatomical envelope, such as a cardiac surface or another surface (e.g., a spherical model at or near the heart surface) between the heart and the outer surface of the patient's body. For example, the segmentation may provide a three-dimensional model or mesh for the body surface and anatomical envelope.

Prior to the EP procedure, the workflow 10 includes involves placing electrodes on the body surface, demonstrated at 16. As mentioned, the process of placing electrodes are placed on the body at 16 can be decoupled from the medical imaging 12 and generation of geometry from such imaging 14. This decoupling is demonstrated by dashed box around the medical imaging 12 and segmentation 14. The electrodes on the body surface can be implemented in various forms. As one example, the electrodes can correspond to a high-density arrangement of body surface sensors (e.g., greater than approximately 200 or more electrodes) that are distributed over and around (e.g., completely circumscribing) a portion of the patient's torso (thorax) for measuring electrical activity associated with the patient's heart. As another example, the array can be a reduced set of electrodes, which does not completely cover the patient's entire torso and is designed for measuring electrical activity for a particular purpose (e.g., an array of electrodes specially designed for analyzing atrial fibrillation and/or ventricular fibrillation) and/or for monitoring electrical activity for a predetermined spatial region of the heart (e.g., atrial region(s) or ventricular region(s)).

After the electrodes have been positioned on the body surface, optical imaging is performed to digitize the electrodes on the body surface, demonstrated at 18. The imaging at 18 can utilize any form of range imaging device, such as a portable optical imaging device disclosed herein, to acquire a series of image frames that correspond to images of the body surface taken at plurality of different viewing angles with respect to the body surface. For instance, the range imaging device has a field of view that can image only a portion of the electrode array in a given image frame. Thus, the imaging device is moved around the patient to image different portions within its field of view until each of the visible parts of the torso surface and associated electrodes have been captured in one or more image frames. In some examples, the entire torso containing electrodes can be digitized via the range imaging device to produce a plurality of image frames that collectively include all electrodes. In other examples, such as where a patient is lying on an EP couch, bed or other surface, during such imaging, the portions of the torso and electrodes within the line of sight of the imaging device are directly imaged over a plurality of image frames, while hidden portions of the torso and electrodes are not included in the image frames.

At 20, a three-dimensional surface geometry of the torso is acquired based on the imaging at 18. For example, the image frames are stitched together and utilized to form a 3D image of the patient's torso including the arrangement of electrodes distributed across the torso. An example of a stitching process that can be implemented to register and combine image frames is demonstrated with respect to FIG. 2. Thus, a complete 3D surface can be constructed from the image frames, in which each image frame is correlated with the previous frames to provide accumulated surface information. The surface geometry provided at 20 may be a single volume mesh such as corresponding to set of point clouds for the surface.

At 22, electrodes are identified. In some examples, the electrodes are identified in the 3D surface geometry provided at 20. In other examples, the electrodes can be identified directly based on image processing of each acquired image frame—either as each frame is acquired or after multiple frames have been acquired. For instance, circular or other predetermined shapes may be segmented from the image to identify electrode locations and a centroid may be used to represent each such electrode location. Additionally or alternatively text or other markers visible to the camera may be printed on the electrode array and recognized via image processing (e.g., using optical character recognition). The resulting set of identified electrodes at 22 may include the full set of electrodes or a partial set, depending on whether any electrodes are hidden—not visible from the complete digitized surface for the torso and electrodes or partial set depending on whether all electrodes have been identified. Within the stitched image, known relationship for the other electrodes (using a known distribution of electrodes) can be used to determine the location of electrodes on the torso surface that were imaged at 18 and included in the stitched torso image and corresponding surface geometry at 20.

In some examples, the identification of electrodes at 22 can be used to provide guidance to the user. For example, in response to determining that one or more expected electrodes have not been identified in the geometry data (at 22), the method 10 can provide an indication (e.g., graphical on a user interface, audible or text) to the user that electrodes are missing from the imaging data and that additional imaging is needed, as show by dotted line 23 returning from 22 back to 18. The indication may specify the missing one or more electrodes by number or an anatomical region of the patient's torso where such missing electrodes are expected to reside based on the placement at 16.

At 24, the location is estimated for any hidden surface geometry and electrodes (e.g., not within the line of sight of the imaging device during image capture at 18). For example, the imaging at 18 can be performed while the patient is in the same position as during the EP procedure, such as lying on a couch or bed. Therefore, during imaging a portion of the electrodes (e.g., on the patient's back) are engaging the bed or other surfaces or otherwise hidden from the line of sight of the camera during image capture. As a result, when a patient is lying down (i.e., supine), electrode location information for hidden electrodes cannot be directly derived from one or more images produced by the optical scanning mechanism. Thus, at 24, the method 10 is implemented to derive the location of hidden electrodes on the back side of the patient, such as by leveraging information from the optical scanning combined with known structure and arrangement of electrodes on the posterior side.

Figure 11:
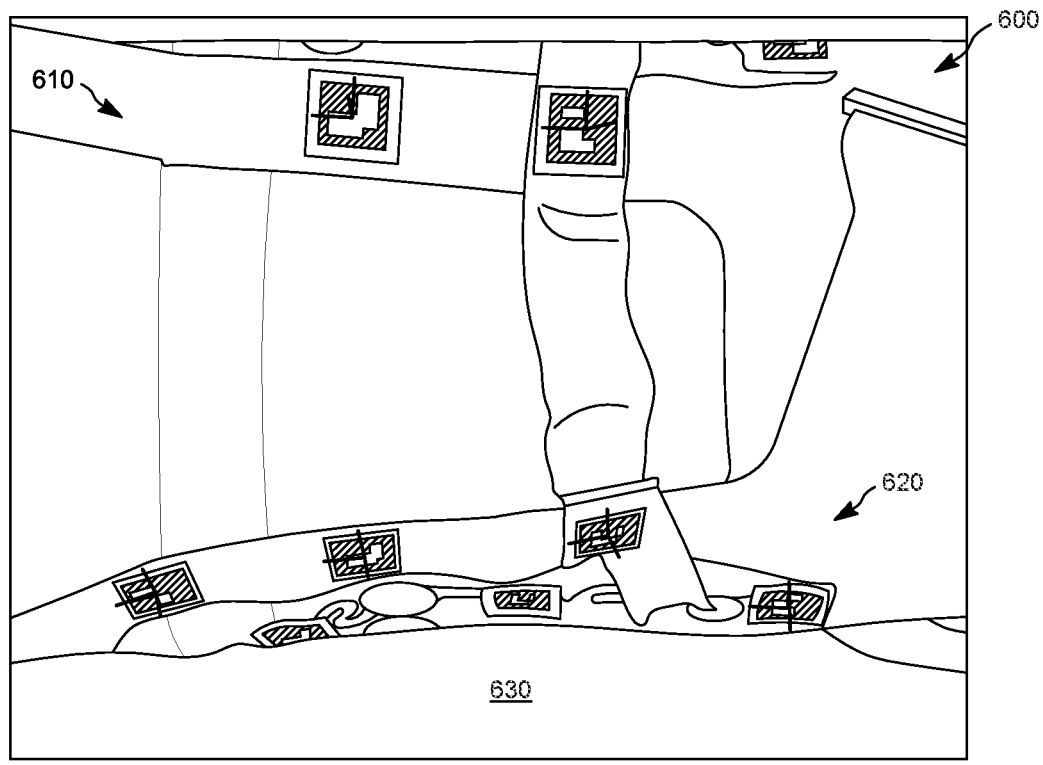
FIG. 11 is a side view depicting an example of anterior and posterior electrode panels attached to a torso while lying down on a table.

By way of example, the optical scanning that is performed at 18 can see electrodes on the side of the patient (see, e.g., FIG. 11). A portion of the electrodes seen on the side of the patient are connected to (i.e., part of) a back panel electrode array. The back panel electrode array may be configured as one integral web of flexible material (e.g., a fabric material panel) to which the electrodes are attached. For example, the panel may be configured to be pliant in transverse direction to facilitate attaching to the patient's back, but not provide for stretching in a planar or lateral direction. Consequently, the panel does not stretch and the electrodes maintain predetermined relative locations on such panel (see, e.g., FIG. 9). The predetermined locations can be stored in memory. Therefore, with some electrodes and/or other markers from the back panel visible on one or both sides of the patient, and at the top of the shoulder area, the 3D locations of the hidden electrodes distributed across the panel between the visible portions of the electrode array may be calculated based on the locations of the back panel electrodes identified at 22 on the side and the predetermined electrode location data. A similar approach may be utilized to compute electrode locations for other electrodes that may be hidden on other portions of the patient's torso.

For example, on a flat EP couch, with no cushion, the back shape will be the continuation of the optically scanned surface until it comes to rest on a flat plane, corresponding to a surface of the EP couch. The 3D location of the flat plane is derived from the optical scans (at 18). That is, the optical scans that include the side of supine positioned individual will record more than just the patient or electrode array, but will also capture the surface (e.g., couch) underneath and supporting the patient. The surface geometry of the hidden flat surface thus may be estimated as a plane in 3D space coincident with the surface of the supporting couch or other structure.

In examples when a cushion is placed under the patient (either between the couch and patient or as part of the couch), the physical compression of the cushion can be calculated to account for the deflection due to the patient weight. For instance, the patient's weight, the size of the patient cross section, and the center of the patient cross section can be input parameters that are used (e.g., as a model) by the estimation at 24 to represent the resulting cushion compression profile, which may be adjusted by a cushion material stiffness setting (e.g. Indentation Load Deflection rating for the foam). The hidden back panel shape thus can be calculated to follow the resulting compressed cushion profile. The calculated back panel surface geometry estimated at 24 is connected to the surface geometry acquired at 20 for the optically visible portions of the surface (e.g., via stitching) to provide complete torso surface geometry and electrode locations for the patient. The surface geometry and electrode locations distributed across the surface geometry can be stored in memory.

At 26, the segmented body surface geometry (from 14) is registered in a 3D coordinate system with the surface geometry and electrode locations derived at 18-24. As one example, the image(s) of the digitized electrodes generated from 20 can be registered into the coordinate system of the segmented body surface geometry that is generated at 14. As another example, the segmented body surface geometry that is generated at 14 can be registered in the coordinate system of the surface generated from the digitization of the electrodes at 24. In yet another example, the generated geometry of 14 and the geometry for the digitized electrodes from 20 can be registered into a different but common three-dimensional coordinate system.

Once the torso surface has been reconstructed from the optical scanning, the surface needs to be correlated with the segmented body surface from the imaging modality (e.g., CT or MRI). There may be differences in the general structure of the two skin surfaces, due to differences between the surfaces on which the patient lies during imaging at 12 and 18. For example, a CT system's couch profile is curved and an EP Lab table is flat. For an accurate registration, and therefore accurate location of the heart relative to the skin, the registration module must take this into account. Alternatively, one of the table surfaces can be modified to the profile of the other.

As an example, the registration at 26 includes a rigid registration to provide a rough alignment between the two skin surfaces, such as using features such as surface centroids and visible body features that do not deform substantially (e.g. shoulders and neighboring bones.) The registration at 26 can then perform a deformable registration to morph one or both of the geometries into further alignment. The registrations are applied to the CT/MRI volume, resulting in a segmented heart or cardiac envelope that is in the same frame of reference as the acquired skin surface and including the electrode locations distributed across the surface.

In some examples, additional geometry information may be utilized to enhance the digitization of electrodes at 18, such as an electromagnetic sensing system (e.g., one of the Aurora tracking systems from Northern Digital, Inc.). In an additional or alternative example, another imaging modality (e.g., fluoroscopy) may be used to identify markers to facilitate registration at 26. For instance, radiographic markers may be placed on or at known locations with respect to predetermined set of electrodes, such as may be out of line of sight from the range imaging device (e.g., electrodes on a patient's back while lying on his/her back). Fluoroscopy or another portable radiographic imaging modality may be used to identify the set of one or more markers on the back panel, or other locations which are hidden as to not be in direct line of sight, during image acquisition. One or more markers are also placed on the front (or other visible locations). Fluoroscopic imaging systems are usually available in EP labs although other medical imaging modalities may be used to detect the markers. Fluoroscopic imaging can be performed, for example, through different angles to determine the 3D location of the markers by back-projection. In some examples, the markers can be of different shapes so that they can be easily differentiated among themselves and with other hardware like catheter electrodes. The markers can be segmented and registered to the image and, because their location is known with respect to the sensor electrode, the registered marker location can be used to estimate sensor locations around the torso.

Once the surfaces from 14 and 24 have been registered together at 26, such that the electrode locations on the body surface and the anatomical envelope are registered in a common coordinate system, corresponding geometry data may be generated and stored in memory for use in an EP procedure at 28. An example of a system that utilizes the geometry data generated using the method 10 is disclosed herein with respect to FIG. 13.

Figure 2:
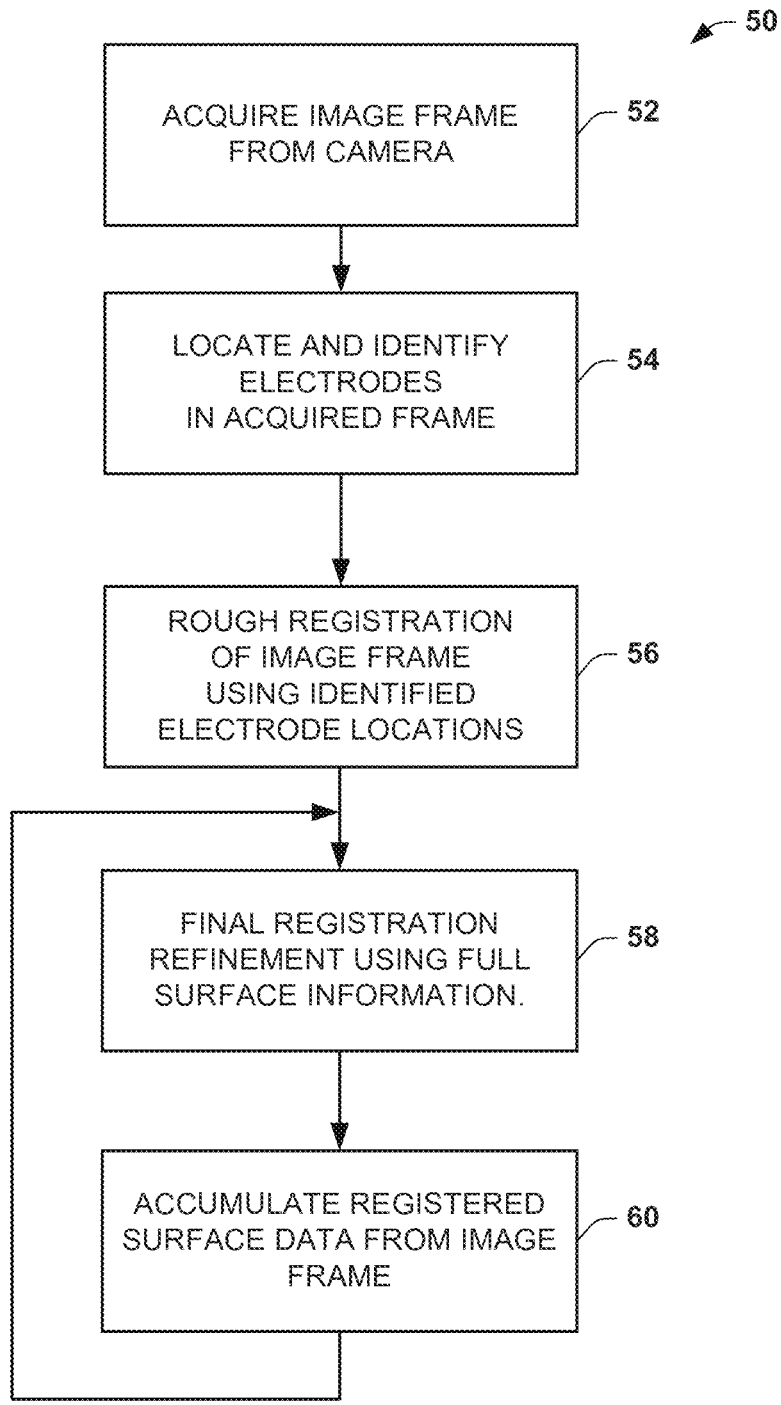
FIG. 2 depicts an example method for image processing to stitch and register a plurality of acquired image frames.

FIG. 2 depicts an example method 50 for image processing to stitch and register a plurality of acquired image frames (e.g., generally corresponding to the imaging 18, geometry acquisition 20 and electrode identification 22 in the method of FIG. 1). That is, to build a complete 3D surface for the full set of electrodes, each image frame needs to be correlated with the other frames. This process of registering and combining the images in the method 50 is referred to herein as 'stitching'. At 52, an image frame is acquired from the camera. For example, the camera is range imaging device (e.g., RGB+D camera) such that the image frame includes RGB and depth information for the visible objects within the camera's field of view. Each of a plurality of such image frames acquired by the imaging device may be stored as image data. The following parts of stitching can be implemented as each subsequent frame is acquired. Alternatively, the method may be performed after the plurality of image frames have been acquired.

Figure 3:
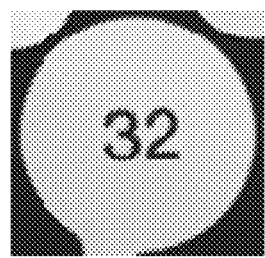
FIG. 3 depicts an example of an electrode containing electrode identifying text.
Figure 4:
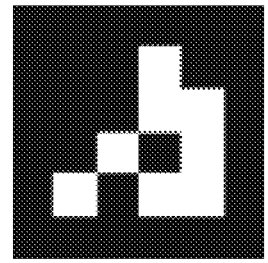
FIG. 4 depicts an example of a tracking marker.
Figure 8:
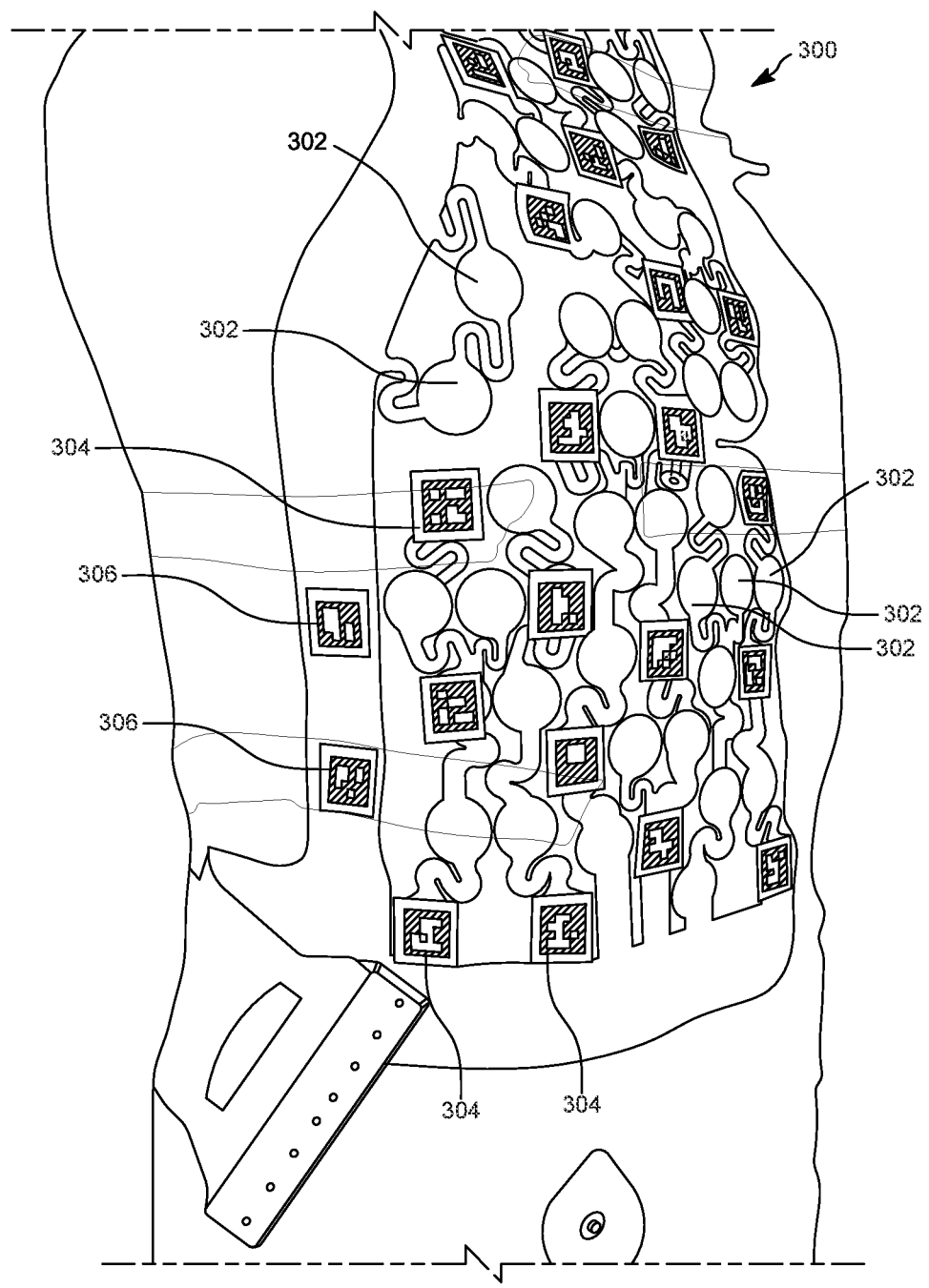
FIG. 8 depicts an example of an electrode array containing tracking markers that is attached to an anterior of a torso.
Figure 9:
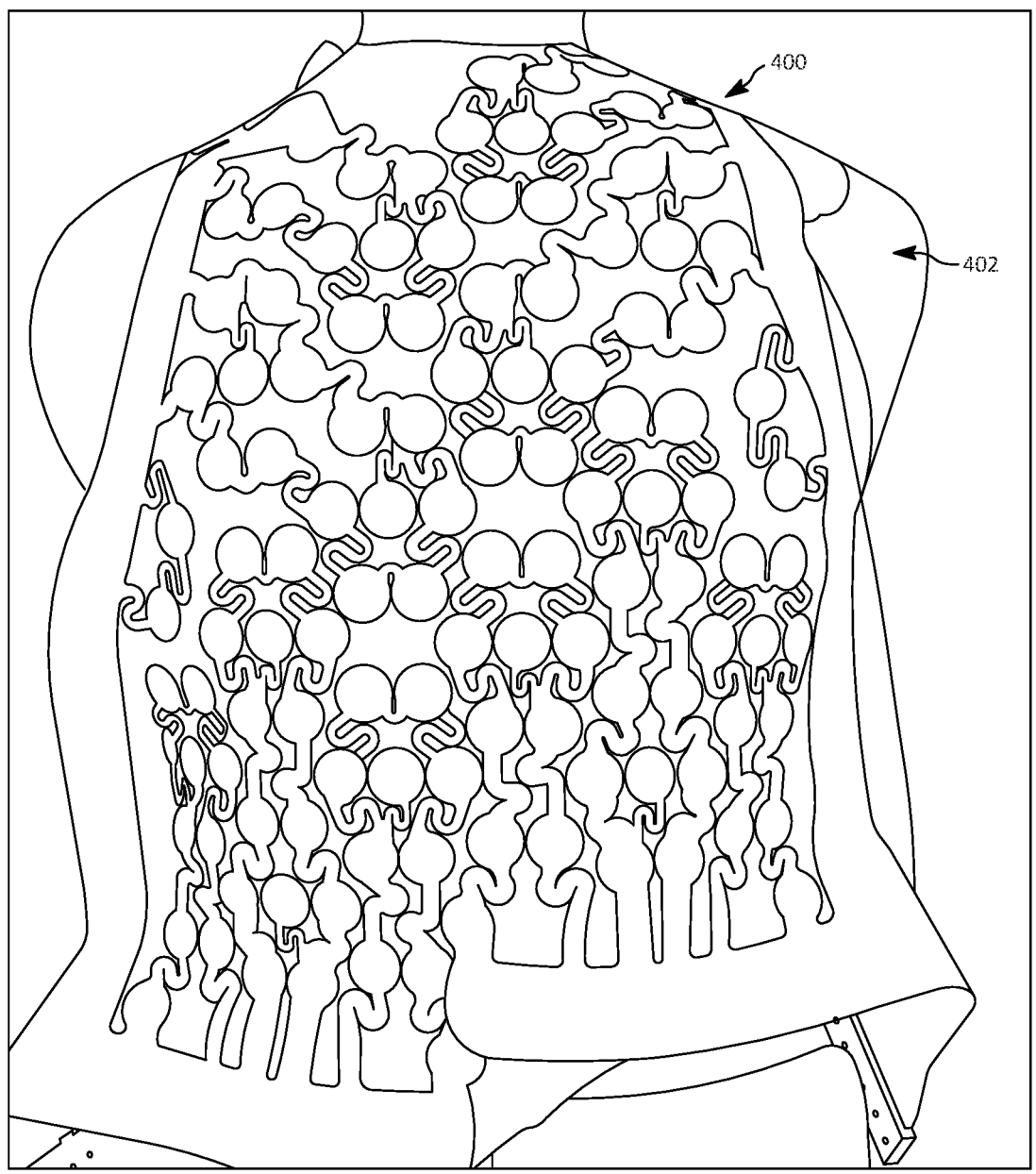
FIG. 9 depicts an example of another electrode array that is attached to the posterior of the torso.
Figure 10:
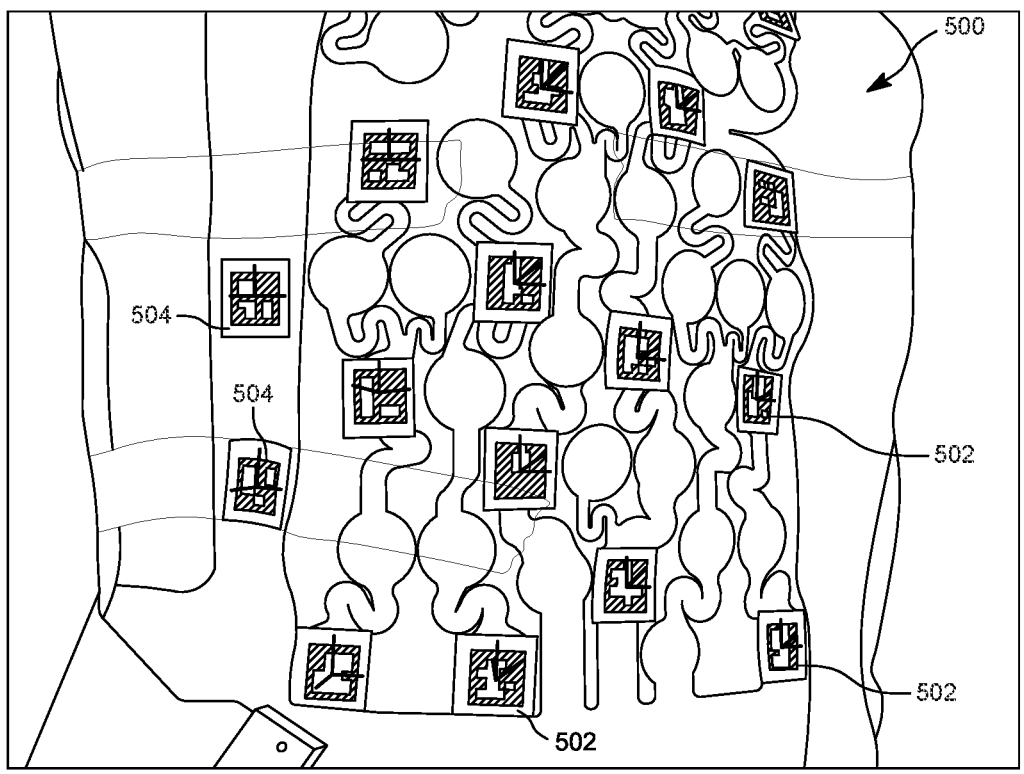
FIG. 10 depicts an example of part of an electrode array containing tracking markers to identify locations of electrodes.

At 54, electrodes in a given acquired image frame are located and identified. The locating and identification for each image frame can be based on visual representations associated with the electrodes. The electrodes have known visual features on the electrode array, which are discernable via automated methods, to enable their identification. For example, the representation can contain text, such as one or more numbers and/or letters printed on the outer surface for each electrode. For example, FIG. 3 shows an electrode with the number "32" printed on a circular-shaped outer layer for an electrode. The circular outer layer is surrounded by a dark substrate layer, which facilitates detecting the boundary of the electrode in optical image data. Other numbers or reference characters may be used, such as shown in FIGS. 8-10. Additionally, or alternatively, the electrode array could be augmented with a unique tracking marker corresponding to each respective electrode, such as a block pattern in a square shown in FIG. 4, which can be printed on the outer layer of a selected set of electrodes. Additionally or alternatively, tracking makers can be positioned at predetermined locations across the outer surface of the electrode array having known spatial locations on the array relative the set of electrodes on the array. The example in FIG. 4 is a block code, although other codes (e.g., bar codes and QRS codes or the like) could be used to identify electrode locations on the array in other examples.

By way of example, to locate the electrodes, at 54, image processing uses the known visual features to search the image frame for the appropriate shape (e.g., circle) or block pattern (e.g. tracking marker). For example the location of each electrode or tracking marker can be defined as a pixel location and depth associated with a center (centroid) of the electrode or tracking marker, respectively. To identify each located electrode, the text in the located electrode can be recognized (e.g., OCR methods) to ascertain its identity. If the text is not discernable for a given electrode, the neighborhood of identifiable electrodes provides sufficient information to determine the identity of the given electrode. When markers are used, each marker's block pattern is encoded with a unique identifier that can be correlated to the electrode(s) it is marking. The location and identity of electrodes can be ascertained for each of the acquired image frames and stored in memory of a computing device.

After the location and identity of electrodes has been determined for at least two image frames, at 56, the method performs an initial rough registration between pairs of image frames using locations of identified electrodes. For example, the locations of identified electrodes in different frames can be aligned as to be spatially overlapping with each other. Errors caused by large camera movements can be mitigated by using such the identified electrodes in the newly acquired frame to perform the alignment with the previously discovered electrodes locations in one or more previous frames. Once all common electrodes in each of the frames have been aligned to provide such rough, initial alignment, the method proceeds to 58.

At 58, final registration refinement is performed using full surface information captured respective image frames. Then, at 60, registered surface data from the image frame is accumulated and stored in memory. For example, surface accumulation is accomplished using a truncated signed distance volume. Surface data for the rough registered view is projected out of the distance volume, to feed into the final registration stage at 58. Thus, from 60, the method returns to 58 for iteratively refining the registration refinement for the next image frame, which has already been roughly aligned at 56. The method 50, for example, may employ iterative closest point for alignment at 58 following the rough initial alignment of two frames at 56. By using the previous frame's alignment as the rough alignment followed by the iterative closest point alignment on the full acquired 3D surface information, helps to ensure that the rough alignment is correctly computed for all frames, while leveraging the full 3D surface alignment to facilitate fine accuracy. This rough alignment at 56 also permits easy restarts of scanning for missing areas, as may be needed, without a need for continuity with previous frames. As mentioned, for example, missing electrodes can be identified in response to determining that one or more electrodes are missing from the full 3D surface based on the set of electrodes identified at 54.

All visible surfaces with electrodes on them should be scanned by a user via the optical camera, to ensure the system has torso electrode locations for generating geometry data for use in solving the inverse problem. Additionally, by identifying the electrodes during the surface scan for each acquired image frame enables the system to guide the user in response to detecting one or more portions of the patient's body have not been scanned. For example, if one or more missing electrodes are identified, the method may generate guidance (e.g., by providing visual and/or audible feedback) to indicate which electrode(s) are missing. If one or more electrode is hidden or otherwise not able to be imaged, the user may enter a user input to ignore such electrode(s) for purposes of providing guidance. The guidance may also include indicating a region of the body surface requires further image scanning based upon the known relative layout of electrodes on the array. In response to acquiring one or more such new images, each newly acquired image (acquired at 52) may be processed according the method 50 and stitched into the full 3D surface image, as described herein. For example, in FIG. 8, if electrodes 25, 28, and 27 are missing from the acquired image frame data, the computing device executing the method 50 can provide visual (and/or audible) feedback to instruct the user to further scan the right breast area with the portable optical imaging device (e.g., camera).

As mentioned, in many instances, the patient is supine on an EP table during the image scans with the optical imaging device such that many electrodes distributed across the patient's back may be hidden. Accordingly, the locations in 3D space of the hidden electrodes need to be estimated as disclosed herein for use in constructing a full 3D surface geometry for the electrodes on the patient's body surface.

Figure 5:
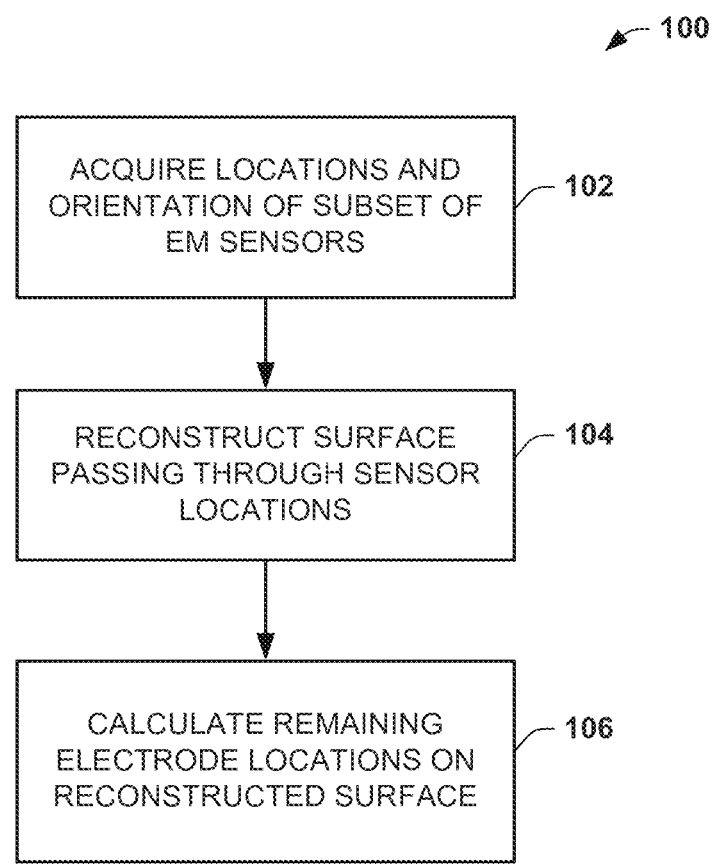
FIG. 5 depicts an example method to estimate the location of hidden electrodes using electromagnetic tracking.

As one example, FIG. 5 depicts a method 100 that can be implemented to estimate the location of hidden electrodes using electromagnetic tracking (e.g., corresponding to the estimation at 24). It is understood that such EM tracking may be used in place of or in addition to the back panel calculation and/or the 3D camera surface acquisition. For example, six degree of freedom (6DOF) sensors can be attached to the electrode array (e.g., integrated on a vest or other form of electrode array) at known locations with respect to the set of electrode locations. The position and orientation of each of the six DOF sensors can be tracked in 3D space in the absence of visibility of such sensors by the range imaging camera. Examples of 6DOF sensors that can be used are commercially available from Northern Digital, Inc. To minimize the number of sensors, sensors do not need to be placed at every electrode, due to the orientation information provided by the 6DOF sensors. In one example, the sensors are located at a portion of the electrodes such as distributed evenly across the back panel electrode array. In another example, sensors need not be co-located with the electrodes. By placing some sensors co-located with some electrodes, the location of such electrodes can be readily determined in 3D space as the same location as the sensor.

At 102, the 3D location and orientation of the 6DOF sensors are determined based on the EM tracking data. In the example where the sensors are co-located with respective electrodes (e.g., some or all), the location and orientation of such identified electrodes can be specified in 3D space as the same location and orientation as the respective sensors. As an example, a tracking system includes a field generator that supplies an EM field to induce current in the sensors on the electrode array. The induced current is provided as tracking signals to tracking system that is configured to compute 3D location and orientation of each of the sensors in a coordinate system of the tracking system.

At 104, a surface passing through the EM sensor locations (and any electrodes co-located with the sensors) is reconstructed. For example, given a known spatial arrangement of the electrodes on the electrode array (e.g., the back panel from the vest design) and surface location with orientation information at a subset of those electrodes co-located with EM sensors, the remaining portion of the surface can be reconstructed to match the tangential information at the known locations corresponding to orientation and tangential information for the tracking data. The surface may be reconstructed as a mesh or other 3D surface construct having nodes at each determined sensor/electrode location specified by the tracking data.

At 106, the remaining electrode locations are calculated on the reconstructed surface. The remaining, unknown electrode locations can be computed using the known relative distances between electrodes in the electrode array and distances across the reconstructed surface with respect to known electrode locations (e.g., as acquired at 102). By way of example, the unknown electrode locations are known to reside on the reconstructed surface (from 104). Since the relative position of all electrodes are known from the electrode array geometry, the relative distances from the known electrodes to the unknown electrodes thus are available from the constraints of the electrode array geometry. Therefore, the location of each unknown electrode can be ascertained as the point where the distance across the surface to the nearest known electrodes matches (within a specified distance tolerance) the known distance between each respective pair of the electrodes.

Figure 6:
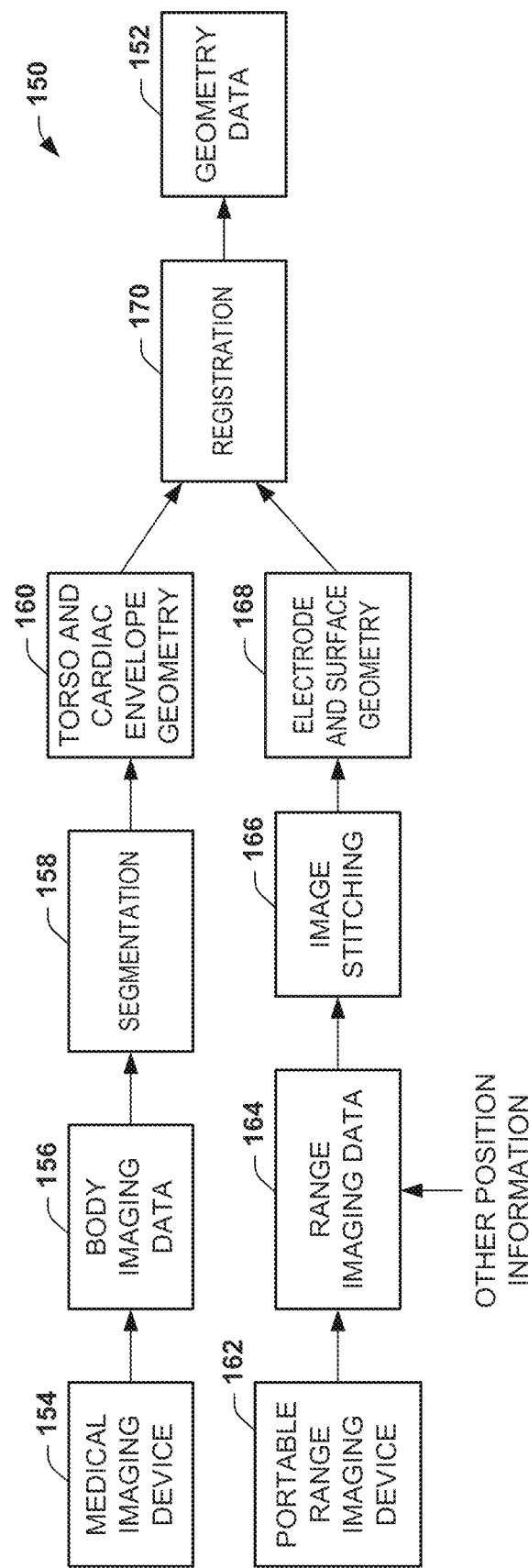
FIG. 6 depicts an example of a system for digitizing electrodes and anatomy to generate geometry data for use in an electrophysiology procedure.

FIG. 6 depicts an example of a system 150 that can be utilized to generate geometry data 152 such as can be utilized in an EP study as disclosed herein. The system 150 includes a medical imaging device 154 that is utilized to generate body imaging data 156. The medical imaging device can implement any one or more imaging modality, such as disclosed herein, which generates the body imaging data including internal structures within a patient's body and body surface. The body imaging data 156 can be stored in memory that is accessible by one or more processors (not shown). The processor can execute instructions, corresponding to methods for performing the functions disclosed herein.

For example, the processor can execute the segmentation method 158 to segment structure from the body imaging data 156. The segmentation can include determining location of the body surface and one or more structure of interest within the patient's body such as the patient's heart. The segmentation 158 can be utilized to generate torso and cardiac envelope geometry 160 that can be stored in memory. The torso and cardiac envelope geometry can correspond to a 2D or 3D mesh or other construct that defines the spatial relationship between the body surface of the torso and the cardiac envelope (the epicardial surface).

The system 150 also includes a range imaging device 162, such as a portable optical range imaging device. The range imaging device 162 is configured to image an outer surface so the patient's body to which an arrangement of electrodes has been placed. The range imaging device 162 thus provides range imaging data 164 corresponding to a set of image frames acquired by the device, which can be stored in memory. In some examples, the range imaging data can also include or be combined with other position information associated with the body surface. For example, the other position information can be generated from electromagnetic tracking system according to the position of tracking sensors attached to the electrodes or a substrate to which the electrodes are connected, such as described with respect to FIG. 5.

The range imaging data 164 includes a set of points in three-dimensional space sufficient to determine the locations for each of the plurality of electrodes that have been positioned on the patient's torso. The range imaging data 164 can include a plurality of image frames that collectively include a sufficient portion of the patient's body from which the entire torso can be determined. For example, each pixel can include an image value (e.g., color value) and depth value). Since there may be overlap between the images from the range imaging data 164, the processor execute instructions to perform image stitching at 166. The image stitching thus can generate a three-dimensional image corresponding to a surface in a single volume mesh. For example, the stitched image generated via the image stitching 166 thus can define a set of point clouds for the patient's body surface on which the electrodes have been placed. For example, the image stitching 166 can implement image processing, such as involving visual SLAM (simultaneous localization and mapping), image registration, and 3D reconstruction (e.g., corresponding to the method 50 of FIG. 2) to provide the electrode and 3D surface geometry 168. For example, the geometry 168 can correspond to a data set that describes a mesh or other spatial construct that describes the spatial relationships among the electrodes, such as represented as points on the body surface. The resulting set of point clouds for the surface constructed by image stitching 166 thus can generate electrode and surface geometry 168. The electrode and surface geometry 168 can be stored as corresponding data in memory as disclosed herein. In the system 150, the torso and cardiac envelope geometry 160 and electrode and service geometry 168 can be decoupled from each other.

The system 150 also includes a registration method 170 (e.g., corresponding to 26 of FIG. 1) that registers the torso and cardiac envelope geometry 160 with the electrode and surface geometry 168 and provide the corresponding geometry data 152. The registration method 170 thus can generate geometry data 152 that includes 3-D spatial geometry locations (e.g., corresponding to points on a mesh) for each of a plurality of electrodes positioned on the patient's body surface and the 3-D spatial geometry locations (e.g., corresponding to points on a mesh) of the cardiac envelope (heart surface). The geometry data 152 thus can be stored in memory and used in conjunction with an EP study, as disclosed herein.

Figure 7:
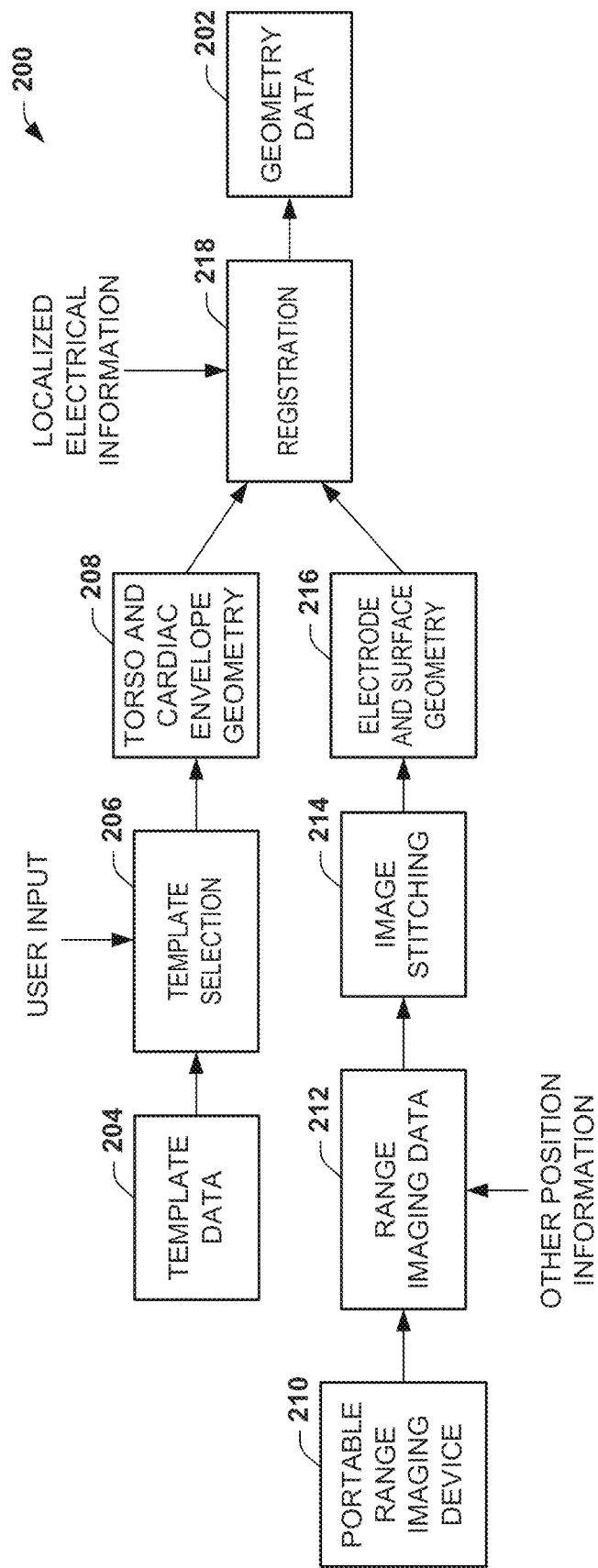
FIG. 7 depicts an example of another system for digitizing electrodes and anatomy to generate geometry data for use in an electrophysiology procedure.

FIG. 7 depicts an example of another system 200 that can be utilized to generate geometry data 202 such as for use in performing an EP study on a patient. The system 200 is similar to that demonstrated in the example of FIG. 2 except that medical imaging is not required to generate torso and cardiac envelope geometry for a patient. In the system 200, template data is stored in memory. The template data can correspond to a plurality of template in a database such as a body of atlases for a plurality of different body shapes. Based upon patient criteria, responsive to a user input, template selection can occur. This can be in response to selecting a particular template for a given patient or adjusting (morphing) the body atlas in response to measurements and other patient demographic information. Template selection can also be enhanced in response to previous medical imaging for a given patient. In response to the template selection and user input the corresponding torso and cardiac envelope geometry can be generated at 208 and stored in memory. Thus in this example, the torso and cardiac envelope geometry may represent a generic or customized model of anatomy that defines a body surface and cardiac envelope (heart surface).

The system 200 also includes a range imaging device 210, such as a portable device. The range imaging device 210 is configured to image an outer surface so the patient's body to which an arrangement of electrodes has been placed. The range imaging device 210 thus provides range imaging data 212 corresponding to a set of image frames acquired by the device, which can be stored in memory. In some examples, the range imaging data 212 can also include or be combined with other position information associated with the body surface, such as disclosed herein (e.g., EM tracking data). The range imaging data 212 includes a set of points in three-dimensional space sufficient to determine the locations for each of the plurality of electrodes that have been positioned on the patient's torso.

As in the example of FIG. 6, the system 200 includes an image stitching method 214 generate a three-dimensional image corresponding to electrode and surface geometry 216, such as a set of point clouds for the patient's body surface on which the electrodes have been placed. The 3D electrode and surface geometry 216 can be stored in memory as disclosed herein.

The system 200 also includes a registration method 218 that is executed to combine the torso and cardiac envelope geometry 208 with the electrode and surface geometry data 116 to generate the geometry data. Since, in some examples, the location of the heart in the generic geometry data 208 may be rough estimate for a given patient, the registration method 218 can be fine tuned in response to localized electrical information obtained from the patient during a registration process. For example, the registration method 218 can be implemented and adjusted during the EP study such as by identifying signal features, such as a QRS complex along a given portion of the patient's heart. In one example, a QRS complex can be detected or known to traverse a given path corresponding to the patient's septum. Since the septum can be spatially identified from the cardiac envelope geometry 208, the location of the patient's heart can be adjusted accordingly through the registration process to more accurately represent an estimate of the heart surface location and orientation in the resulting 3D geometry data 202.

For example, the QRS complex can be monitored over a period of time (e.g., 15 milliseconds) for a plurality of points to determine the septum location for the patient's heart. Once the location of the septum has been identified within the patient's body, the cardiac envelope geometry and location of the patient's heart represented in the geometry data 202 can be adjusted to match the coordinates of the septum along which the QRS signals travel. As a further example, the QRS signal can be localized as dipole within the patient's body to arrange and reposition the location of the heart represented in the geometry data 202. While the above describes the QRS complex as an example of the localized electrical information, it is understood that any organized pattern may be utilized and located in the patient's heart to adjust the heart surface location represented in the geometry data. Thus the localized organized pattern can be used to shift or adapt the heart model based on the location determined for the organized pattern.

In each of the example systems of FIGS. 6 and 7, the range imaging device and resulting data may be replaced by a monoscopic imaging device and corresponding imaging data that is generated. For example, markers may be applied at known locations with respect to the electrode, such as shown in the examples of FIGS. 8, 10 and 11. The monoscopic imaging device may be used to generate image data that includes series of images of the electrodes and markers at different angles for the line of sight of the monoscopic imaging device. In this example imaging approach (using markers in conjunction monoscopic imaging), depth information for the pixels in the image data can be derived at the center of the markers. This depth information (at center or other marker locations) in combination with pixels throughout the image data can be utilized to construct (through image stitching) a three-dimensional image corresponding to the electrode and surface geometry 168, 216, such as a set of point clouds for the patient's body surface on which the electrodes have been placed. The electrode and surface geometry can be stored in memory and registered with torso and cardiac envelope geometry as disclosed herein.

FIG. 8 depicts an example of an electrode array 300 that is attached to an anterior of a patient torso model. For example, the array 300 is configured to attach to the right torso of the patient. Another array (not shown) would be configured to attach to the left torso. The array demonstrated in FIG. 8 includes a plurality of electrodes 302 and a set of tracking markers 304 distributed at known locations of a web of flexible substrate material. In this example, at least some of the tracking markers 304 are co-located, overlying a subset of the electrodes 302. Thus, the 3D location of the tracking markers 304 are determined from the acquired image frames, as disclosed herein. The tracking markers 304 encode respective electrodes that can be located and identified based on the determined location of each tracking marker. The location of remaining electrodes (not co-located with tracking markers) can be determined based on the acquired location of the tracking markers and the known relative location of the electrodes across the array. Other tracking markers 306 may be located with other parts of the array 300, such as to identify edges or other predetermined locations of the array.

FIG. 9 depicts an example of another electrode array (e.g., a back panel electrodes) 400 that is attached to a posterior of the torso 402 (e.g., to cover the patient's back and perhaps some of the side). Each of the electrodes (e.g., numbered 127-252) has a known spatial location with respect to the array 400. Thus, by determining the position of a portion of the electrodes and/or the substrate carrying the electrodes via range and/or monoscopic imaging, the 3D spatial location of the remaining electrodes may be estimated as disclosed herein.

FIG. 10 depicts an example of a portion of another electrode array 500 (e.g., corresponding to right-front side panel electrodes). In this example, a plurality of tracking markers 502 are co-located with respective identified electrodes and are annotated to specify a unique identifier for respective electrodes as well as provide orientation information determined for each such tracking marker (e.g., a 3D Cartesian coordinate system). Some tracking markers 504 also may be placed along one or more side edges of the array to facilitate identifying the array position when the portable imaging device is positioned capture images from other viewing angles. By determining the position of a portion of the electrodes via range and/or monoscopic imaging, the 3D spatial location of the remaining electrodes may be estimated as disclosed herein.

As a further example, FIG. 11 is a side view depicting an example of an arrangement of electrodes (an array) 600 showing both anterior and posterior electrode panels 610 and 620, respectively, attached to a torso while lying down on a table 630. From this viewing angle, the imaging device can locate tracking markers on both panels 610 and 620. One or more electrodes on each panel also may be visibly identifiable from this viewing angle and thereby enable reconstruction of a full 3D surface geometry of the electrodes on the body surface.

Figure 12:
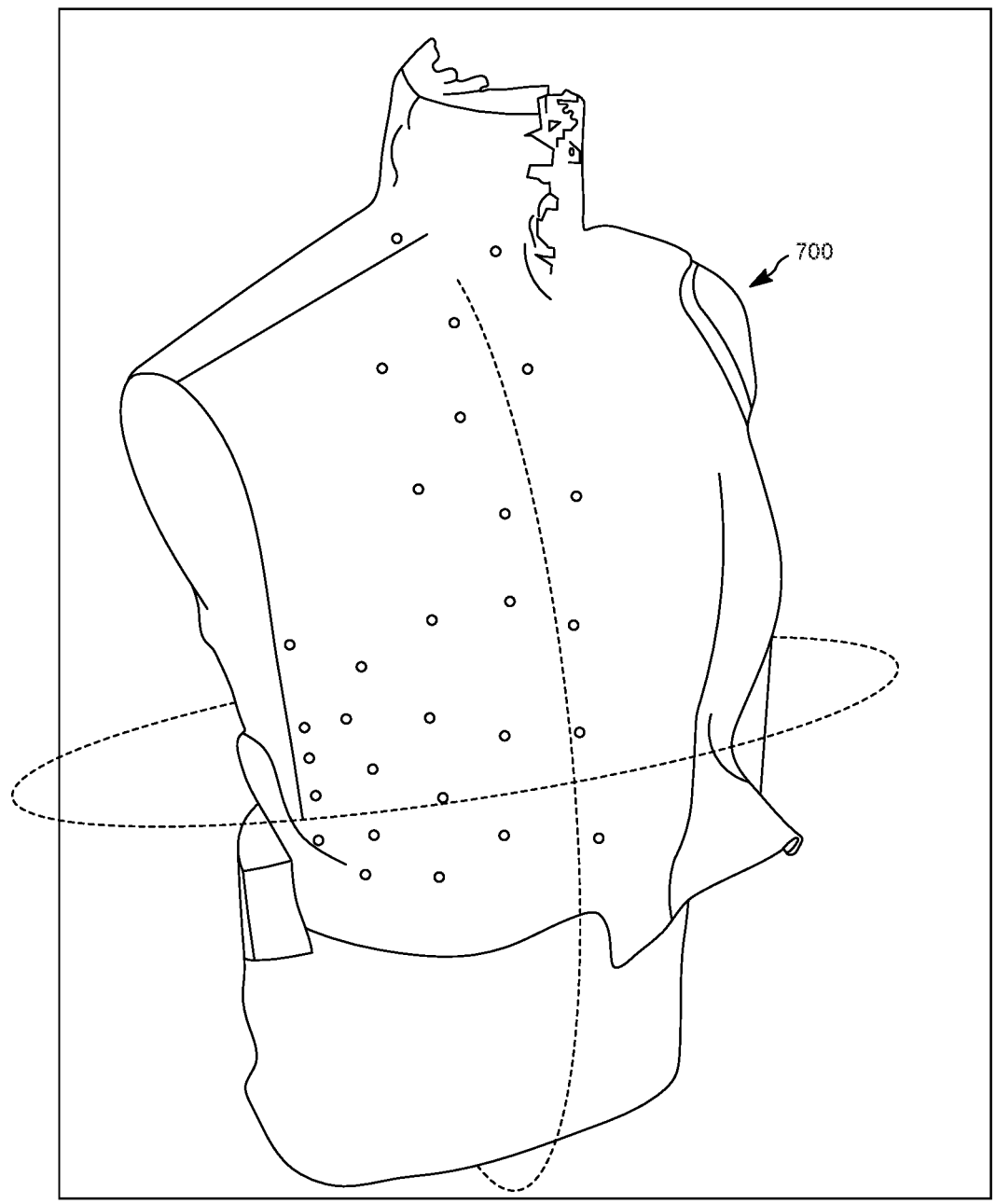
FIG. 12 depicts an example of a reconstructed three-dimensional surface model of a torso showing electrode marker locations.

FIG. 12 depicts an example of a partial reconstructed three-dimensional surface model 700 of a torso showing electrode marker locations for an electrode array (e.g., electrodes on a patient's right front torso electrode panel). In this example, locations of electrodes are noted as nodes at corresponding 3D positions, as determined according to the systems and methods herein. The electrode geometry across the body surface can be registered with the body surface and cardiac envelope geometry computed (by a processing device) based on image data acquired via another imaging modality to generate geometry data for use in performing an EP procedure that employs non-invasive electrical measurements from the electrodes to reconstruct cardiac electrical activity on the cardiac envelope.

Figure 13:
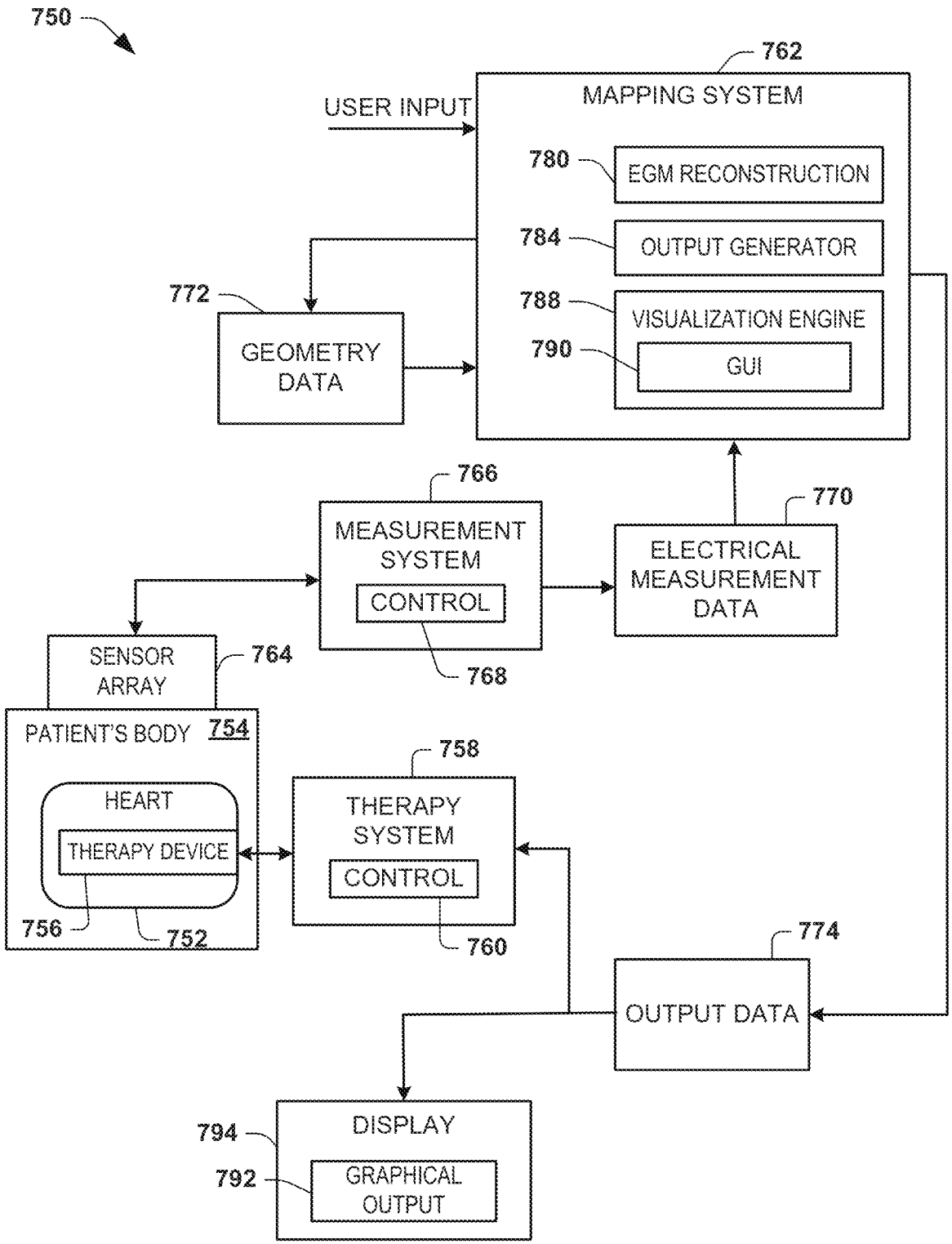
FIG. 13 depicts an example of a mapping and treatment system.

FIG. 13 depicts an example of a system 750 that can be utilized for performing medical testing (diagnostics, screening and/or monitoring) and/or treatment of a patient. In some examples, the system 750 can be implemented to generate corresponding electrocardiographic maps for a patient's heart 752 in real time as part of a diagnostic procedure (e.g., an electrophysiology study) to help assess the electrical activity and identify arrhythmia drivers for the patient's heart. Additionally or alternatively, the system 750 can be utilized as part of a treatment procedure, such as to help a physician determine parameters for delivering a therapy to the patient (e.g., delivery location, amount and type of therapy) based on one or more identified connected trajectories.

In an example where therapy is to be delivered to the patient's heart during such procedure, a catheter having one or more therapy delivery devices 756 affixed thereto can be inserted into a patient's body 754 as to contact the patient's heart 752, endocardially or epicardially. The placement of the therapy delivery device 756 can be guided by various localization techniques and electrical information associated with the patient's heart. Those skilled in the art will understand and appreciate various type and configurations of therapy delivery devices 756 that can be utilized, which can vary depending on the type of treatment and the procedure. For instance, the therapy device 756 can be configured to deliver electrical therapy, chemical therapy, sound wave therapy, thermal therapy or any combination thereof.

As one example, the therapy delivery device 756 can include one or more electrodes located at a tip of an ablation catheter configured to generate heat for ablating tissue in response to electrical signals (e.g., radiofrequency energy) supplied by a therapy system 758. In other examples, the therapy delivery device 756 can be configured to deliver cooling to perform ablation (e.g., cryogenic ablation), to deliver chemicals (e.g., drugs), ultrasound ablation, high-frequency ablation, or a combination of these or other therapy mechanisms. In still other examples, the therapy delivery device 756 can include one or more electrodes located at a tip of a pacing catheter to deliver electrical stimulation, such as for pacing the heart, in response to electrical signals (e.g., pacing pulses) supplied by the therapy system 758. Other types of therapy can also be delivered via the therapy system 758 and the invasive therapy delivery device 756 that is positioned within the body.

As a further example, the therapy system 758 can be located external to the patient's body 754 and be configured to control therapy that is being delivered by the device 756. For instance, the therapy system 758 includes controls (e.g., hardware and/or software) 760 that can communicate (e.g., supply) electrical signals via a conductive link electrically connected between the delivery device (e.g., one or more electrodes) 756 and the therapy system 758. The control system 760 can control parameters of the signals supplied to the device 756 (e.g., current, voltage, repetition rate, trigger delay, sensing trigger amplitude) for delivering therapy (e.g., ablation or stimulation) via the electrode(s) 754 to one or more location of the heart 752. The control circuitry 760 can set the therapy parameters and apply stimulation based on automatic, manual (e.g., user input) or a combination of automatic and manual (e.g., semiautomatic) controls, which may be based on the detection and associated characteristics of connected trajectories on the cardiac envelope. One or more sensors (not shown) can also communicate sensor information from the therapy device 756 back to the therapy system 758. The position of the device 756 relative to the heart 752 can be determined and tracked intraoperatively via an imaging modality (e.g., fluoroscopy, x-ray), a mapping system 762, direct vision or other localization system. The location of the device 756 and the therapy parameters thus can be combined to determine and control corresponding therapy parameter data.

In the example of FIG. 13, a sensor array 764, as disclosed herein, includes one or more electrodes that can be utilized for recording patient electrical activity. The sensing electrodes that form the array 764 can be mounted to a substrate (e.g., a wearable garment), be applied in strips of sensing electrodes or individually mounted electrodes. As one example, the sensor array 764 can correspond to a high-density arrangement of body surface sensors (e.g., greater than approximately 200 electrodes) that are distributed over a portion of the patient's torso for measuring electrical activity associated with the patient's heart (e.g., as part of an electrocardiographic mapping procedure). An example of a non-invasive sensor array that can be used is shown and described in International application No. PCT/US2009/063803, filed 10 Nov. 2009, which is incorporated herein by reference. Other arrangements and numbers of sensing electrodes can be used as the sensor array 764. As an example, the array can be a reduced set of electrodes, which does not cover the patient's entire torso and is designed for measuring electrical activity for a particular purpose (e.g., an array of electrodes specially designed for analyzing atrial fibrillation and/or ventricular fibrillation) and/or for monitoring electrical activity for a predetermined spatial region of the heart (e.g., atrial region(s) or ventricular region(s)).

One or more sensors may also be located on the device 756 that is inserted into the patient's body. Such sensors can be utilized separately or in conjunction with the non-invasive sensors 764 for mapping electrical activity for an endocardial surface, such as the wall of a heart chamber, as well as for an epicardial surface. Additionally, such electrode can also be utilized to help localize the device 756 within the heart 752, which can be registered into an image or map that is generated by the system 750. Alternatively, such localization can be implemented in the absence of emitting a signal from an electrode within or on the heart 752.

In each of such example approaches for acquiring patient electrical information, including non-invasively or a combination of invasive and non-invasive sensing, the sensor array(s) 764 provide the sensed electrical information to a corresponding measurement system 766. The measurement system 766 can include appropriate controls and associated circuitry 768 for providing corresponding electrical measurement data 770 that describes electrophysiological signals detected by the sensors in the body surface sensor array 764. The measurement data 770 can include analog and/or digital information.

The measurement control 768 can also be configured to control the data acquisition process (e.g., sample rate, line filtering) for measuring electrical activity and providing the measurement data 770. In some examples, the control 768 can control acquisition of measurement data 770 separately from the therapy system operation, such as in response to a user input. In other examples, the measurement data 770 can be acquired in real time concurrently with and in synchronization with delivering therapy by the therapy system 758, such as to detect electrical activity of the heart 752 that occurs in response to applying a given therapy (e.g., according to therapy parameters). For instance, appropriate time stamps can be utilized for indexing the temporal relationship between the respective measurement data 770 and therapy parameters use to deliver therapy as to facilitate the evaluation and analysis thereof.

The mapping system 762 is programmed (e.g., instructions stored in non-transitory memory executable by one or more processing devices) to combine the measurement data 770 corresponding to electrical activity of the heart 752 with geometry data 772 (e.g., corresponding to geometry data determined at 26 in the method 10 and geometry data 152, 202) by applying appropriate processing and computations to provide corresponding output data 774. As an example, the output data 774 can include one or more graphical maps demonstrating determined electrical activity that is reconstructed with respect to a geometric surface (a cardiac envelope) of the patient's heart 752 (e.g., information derived from electrical measurements superimposed on a surface of the heart 752).

For example, electrogram reconstruction 780 can be programmed to compute an inverse solution and provide corresponding reconstructed electrograms based on the non-invasive electrical measurement data 770 and the geometry data 772. The reconstructed electrograms thus can correspond to electrocardiographic activity across a cardiac envelope, and can include static (three-dimensional at a given instant in time), over one or more time intervals and/or be dynamic (e.g., four-dimensional map that varies over time). Examples of inverse algorithms that can be implemented by electrogram reconstruction 780 include those disclosed in U.S. Pat. Nos. 7,983,743 and 6,772,004. The EGM reconstruction 780 thus can reconstruct the body surface electrical activity measured via the sensor array 764 onto a multitude of locations on a cardiac envelope (e.g., greater than 1000 locations, such as about 2000 locations or more.

As disclosed herein, the cardiac envelope can correspond to a three dimensional surface geometry corresponding to a patient's heart, which surface can be epicardial or endocardial. Alternatively or additionally, the cardiac envelope can correspond to a geometric surface that resides between the epicardial surface of a patient's heart and the outer surface of the patient's body where the electrodes that form the sensor array 764 has been positioned. Additionally, the geometry data 772 that is utilized by the electrogram reconstruction 780 can correspond to electrode locations determined according to methods and systems disclosed herein. The cardiac envelope defined in the geometry data may be actual patient anatomical geometry, a preprogrammed generic model or a combination thereof (e.g., a model/template that is modified based on patient anatomy), such as disclosed herein.

As an example, the geometry data 772 represents the geometry relationship between the cardiac envelope (e.g., cardiac surface) and the electrodes positioned on the torso surface in a three-dimensional coordinate system. As described herein, the geometry relationship between cardiac envelope and torso surface can be obtained via 3D medical imagining modality, such as CT or MRI, which is performed in the absence of the sensor array 764 being placed on patient. A range imaging camera (e.g., a portable, handheld RGB-D camera) may be utilized to capture a plurality of image frames that are stitched together to digitize the electrodes position on the patient's torso and provide a set of point clouds for the body surface including electrode locations. The electrode and surface geometry data and anatomical data for the cardiac envelope and torso surface are registered together to provide the geometry data 772, as disclosed herein.

As mentioned above, the geometry data 772 can correspond to a mathematical model, such as can be a generic model or a model that has been constructed based on image data for the patient. Appropriate anatomical or other landmarks, including locations for the electrodes in the sensor array 764 can be identified in the geometry data 772 to facilitate registration of the electrical measurement data 770 and performing the inverse method thereon. The identification of such landmarks can be done manually (e.g., by a person via image editing software) or automatically (e.g., via image processing techniques). By way of further example, the range imaging and generation of the geometry data 772 may be performed before or concurrently with recording the electrical activity that is utilized to generate the electrical measurement data 770 or the imaging can be performed separately (e.g., before or after the measurement data has been acquired). In some examples, the electrical measurement data 770 may be processed by the mapping system to extract localized organized patterns of activity to adjust (refine) the geometry data 772 over a period of one or more time intervals (e.g., where a model or template is used to provide initial geometry data).

Following (or concurrently with) determining electrical potential data (e.g., electrogram data computed from non-invasively or from both non-invasively and invasively acquired measurements) across the geometric surface of the heart 752, the electrogram data can further undergo signal processing by mapping system 762 to generate the output data 774, which may include one or more graphical maps. The mapping system 762 can include one or more methods programmed to characterize the electrical information across the cardiac envelope. For example, an output generator 784 can be programmed to generate one or more graphical outputs (e.g., waveforms, electroanatomic maps or the like) for visualization on a display device 794 based on the output data 774. A visualization engine 788 can control features of the output being displayed. For instance, parameters associated with the displayed graphical output, corresponding to an output visualization of a computed map or waveform, such as including selecting a time interval, temporal and spatial thresholds, as well as the type of information that is to be presented in the display 794 and the like can be selected in response to a user input via a graphical user interface (GUI) 790. For example, a user can employ the GUI 790 to selectively program one or more parameters (e.g., temporal and spatial thresholds, filter parameters and the like) utilized by the one or more methods used to process the electrical measurement data 770. The mapping system 762 thus can generate corresponding output data 774 that can in turn be rendered as a corresponding graphical output 792 in a display device 794. For example, the output generator 784 can generate electrocardiographic maps and other output visualizations 792 in the display 794.

Since the measurement system 766 can measure electrical activity of a predetermined region or the entire heart concurrently (e.g., where the sensor array 764 covers the entire thorax of the patient's body 754), the resulting output data (e.g., visualizing attributes of identified stable rotors and/or other electrocardiographic maps) 774 thus can also represent concurrent data for the predetermined region or the entire heart in a temporally and spatially consistent manner. The time interval for which the output data/maps are computed can be selected based on user input (e.g., selecting a timer interval from one or more waveforms). Additionally or alternatively, the selected intervals can be synchronized with the application of therapy by the therapy system 758.

Additionally, in some examples, the output data 774 can be utilized by the therapy system 758. For instance, the control system 760 may implement fully automated control, semi-automated control (partially automated and responsive to a user input) or manual control based on the output data 774. In some examples, the control 760 of the therapy system 758 can utilize the output data 774 to control one or more therapy parameters. As an example, the control 760 can control delivery of ablation therapy to a site of the heart (e.g., epicardial or endocardial wall) based on one or more arrhythmia drivers identified by one or more method(s). In other examples, an individual can view the map generated in the display to manually control the therapy system, such as using the identification location of connected trajectories (e.g., the region between connected trajectories) on the graphical map as a treatment site. Other types of therapy and devices can also be controlled based on the output data 774 and corresponding graphical map 792.

In view of the foregoing structural and functional description, those skilled in the art will appreciate that portions of the systems and method disclosed herein may be embodied as a method, data processing system, or computer program product such as a non-transitory computer readable medium. Accordingly, these portions of the approach disclosed herein may take the form of an entirely hardware embodiment, an entirely software embodiment (e.g., in a non-transitory machine readable medium), or an embodiment combining software and hardware. Furthermore, portions of the systems and method disclosed herein may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in non-transitory computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of structures, components, or methods, but one of ordinary skill in the art will recognize that many further combinations and permutations are possible. Accordingly, the invention is intended to embrace all such alterations, modifications, and variations that fall within the scope of this application, including the appended claims. Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. A method comprising:
   placing a set of electrodes on a body surface of a patient's body;
   digitizing locations for visible electrodes on the body surface based on one or more image frames using range imaging and/or monoscopic imaging;
   estimating locations for hidden ones of the electrodes on the body surface not visible during the range imaging and/or monoscopic imaging;
   registering the locations for the visible and hidden ones of the electrodes on the body surface with predetermined geometry information that includes the body surface and an anatomical envelope within the patient's body; and
   storing geometry data in non-transitory memory based on the registration, the geometry data defining spatial relationships between the set of electrodes and the anatomical envelope.

2. The method of claim 1, wherein at a time prior to placing the electrodes on the body surface, the method further comprises:
   performing three-dimensional medical imaging on the patient's body; and
   generating the predetermined geometry information based on the medical imaging.

3. The method of claim 1, wherein the predetermined geometry information further comprises a template corresponding to an atlas that defines geometry relationships among internal and external anatomical features.

4. The method of claim 3, further comprising selecting the template from a plurality of templates in response to a user input.

5. The method of claim 3, further comprising using localized electrical information measured via at least some of the plurality of electrodes to adjust the geometry relationships among at least some of the internal and external anatomical features.

6. The method of claim 5, wherein the localized electrical information comprises a predetermined organized pattern of electrical activity that is measured from the patient's body over a time interval and travels along an anatomical path that is known with respect to the anatomical envelope.

7. The method of claim 1, wherein estimating the location of the hidden electrodes further comprises:
   storing predetermined electrode geometry data describing a relative spatial position of at least the hidden electrodes, at least one visible electrode or tracking marker that is visible during the range imaging and/or monoscopic imaging being included in the predetermined electrode geometry data; and
   determining a three-dimensional location for the at least one visible electrode or tracking marker,
   wherein three-dimensional locations for the hidden electrodes are estimated based on the determined three-dimensional location for the at least one visible electrode or tracking marker and the predetermined electrode geometry data.

8. The method of claim 1, wherein estimating the location of the hidden electrodes further comprises:
performing range imaging to generate range imaging data for the set of the electrodes within direct line of sight during the range imaging and/or monoscopic imaging;
performing radiographic imaging or electromagnetic tracking to generate other data describing three-dimensional locations of the hidden electrodes out of direct line of sight during the range imaging and/or monoscopic imaging; and
registering the other data with the range imaging data to provide the three-dimensional locations for the electrodes and associated surface geometry.

9. The method of claim 1, further comprising:
acquiring a plurality of image frames from different viewing angles using the range imaging and/or monoscopic imaging; and
stitching the plurality of image frames together to provide a combined image by correlating multiple image frames based on a location and identity of electrodes in the multiple image frames.

10. The method of claim 9, wherein each image frame includes electrodes and surface information within a line of sight of an imaging device that is performing the range imaging and/or monoscopic imaging, the stitching further comprising:
using locations of identified electrodes to perform a rough alignment among the multiple image frames; and
performing a final registration between the multiple image frames based on pixel values and depth information across the surface that is shared by the respective multiple images; and
accumulating registered surface data from each of the image frames according to the final registration.

11. The method of claim 9, further comprising generating guidance to a user by specifying electrodes and/or location information missing from the plurality of image frames based on the location and identity of electrodes determined for the plurality of image frames.

12. The method of claim 1, further comprising:
measuring electrical signals from the body surface using the electrodes;
storing electrical measurement data representing the measured electrical signals over one or more time intervals; and
reconstructing electrical signals onto the anatomical envelope based on the electrical measurement data and the geometry data; and
generating an output visualization on a display based on the electrical measurement data and the geometry data.

13. A system comprising:
an image acquisition system comprising a portable range imaging device and/or monoscopic imaging device configured to generate imaging data containing one or more image frames of a body surface of a patient including a plurality of electrodes that have been positioned on the body surface and in direct line of sight during image capture by the range imaging device and/or monoscopic imaging device;
non-transitory memory to store machine readable instructions and data, the data comprising predetermined geometry information for an internal cardiac envelope and the body surface;
at least one processor to access the memory and execute the instructions to perform a method that comprises:
determining three-dimensional electrode locations and surface geometry from the imaging data, the determined three-dimensional electrode locations and surface geometry including estimated locations for hidden electrodes outside of the direct line of sight during image capture by the portable range imaging device and/or monoscopic imaging device;
registering the determined three-dimensional electrode locations and surface geometry with the predetermined geometry information for the cardiac envelope and the body surface to provide aggregate geometry data describing a three-dimensional spatial relationship between each of the plurality of electrodes and the cardiac envelope; and
storing the aggregate geometry data in the memory.

14. The system of claim 13, further comprising tracking markers at predetermined locations with respect to a portion of the electrodes, wherein the image acquisition system generates a series of image frames that includes the tracking markers, wherein the processor is configured to access the memory and execute the instructions to further determine the electrode locations and surface geometry from the series of image frames based on recognizing the tracking markers in the series of image frames.

15. The system of claim 13, further comprising a radiographic imaging device that generates radiographic imaging data that includes the hidden electrodes out of direct line of sight of the range imaging device and/or monoscopic imaging device,
wherein the processor is further configured to access the memory and execute the instructions to register the radiographic imaging data with the three-dimensional electrode locations and surface geometry determined from the imaging data to provide registered imaging data that is further registered with the predetermined geometry information for the cardiac envelope and the body surface to provide the aggregate geometry data.

16. The system of claim 13, further comprising an electromagnetic tracking system to generate tracking data describing three-dimensional locations of electromagnetic sensors co-located with at least some of the hidden electrodes,
wherein the processor is further configured to access the memory and execute the instructions to register the tracking data with the three-dimensional electrode locations and surface geometry determined from the imaging data to provide corresponding registered data that is further registered with the predetermined geometry information for the cardiac envelope and the body surface to provide the aggregate geometry data.

17. The system of claim 13, wherein the imaging data includes a plurality of image frames acquired from different viewing angles, and
wherein the processor is further configured to access the memory and execute the instructions to stitch the plurality of image frames together to provide a combined image by correlating multiple image frames based on a location and identity of electrodes in the multiple image frames.

18. The system of claim 17, wherein each image frame includes electrodes and surface information within a line of sight of the range imaging device and/or monoscopic imaging device during image acquisition thereby, the processor is further configured to:

perform a rough alignment among the multiple image frames by aligning locations of identified electrodes in the image frames; and perform a final registration between the multiple image frames based on pixel values and depth information across the surface that is shared by the multiple images; and accumulate registered surface data from each of the plurality of image frames according to the final registration.

19. The system of claim 13, wherein the predetermined geometry information further comprises a template corresponding to an atlas that defines spatial relationships among internal and external anatomical features.

20. The system of claim 13, further comprising:

an arrangement of sensors, which includes the plurality of electrodes, configured to surround a thorax when placed on the body surface to non-invasively measure electrical activity from the body surface; and a measurement system to control measurements by the sensors and to provide electrical measurement data representing the measured electrical activity over one or more time intervals, the electrical measurement data including measured and/or reconstructed electrophysiological signals at a plurality of nodes distributed across the cardiac envelope for one or more of time intervals, wherein the at least one processor is further programmed to:

access the aggregate geometry data and the electrical measurement data;

reconstruct electrical signals onto the cardiac envelope; and display a graphical output visualization based on the aggregate geometry data and the electrical measurement data.

* * * * *